United States Patent
Wichelecki (10) Patent No.: US 12,319,949 B2
(45) Date of Patent: Jun. 3, 2025

(54) ENZYMATIC PRODUCTION OF MANNOSE

(71) Applicant: BONUMOSE, INC., Charlottesville, VA (US)

(72) Inventor: Daniel Joseph Wichelecki, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 798 days.

(21) Appl. No.: 17/429,104

(22) PCT Filed: Feb. 11, 2020

(86) PCT No.: PCT/US2020/017708
§ 371 (c)(1),
(2) Date: Aug. 6, 2021

(87) PCT Pub. No.: WO2020/167796
PCT Pub. Date: Aug. 20, 2020

(65) Prior Publication Data
US 2022/0127653 A1  Apr. 28, 2022

Related U.S. Application Data

(60) Provisional application No. 62/804,426, filed on Feb. 12, 2019.

(51) Int. Cl.
*C12P 19/02* (2006.01)
*A23L 33/125* (2016.01)

(52) U.S. Cl.
CPC ............ *C12P 19/02* (2013.01); *A23L 33/125* (2016.08); *A23V 2002/00* (2013.01)

(58) Field of Classification Search
None
See application file for complete search history.

(56) References Cited

FOREIGN PATENT DOCUMENTS

| WO | 2018/129275 A1 | 7/2018 | |
| WO | WO-2018169957 A1 * | 9/2018 | ........... C12N 9/1051 |

OTHER PUBLICATIONS

Tóth, Á., et al. "Plant polysaccharide degrading enzyme system of Thermobifida cellulosilytica TB100 T revealed by de novo genome project data." Acta Alimentaria 46.3 (2017): 323-335. (Year: 2017).*
Sharma V, Ichikawa M, Freeze HH. Mannose metabolism: more than meets the eye. Biochem Biophys Res Commun. Oct. 17, 2014; 453(2):220-8. doi: 10.1016/j.bbrc.2014.06.021. Epub Jun. 12, 2014. PMID: 24931670; PMCID: PMC4252654. (Year: 2014).*
Database Uniport Hydrolase_A0A147KII8. Jun. 8, 2016.
Huang et al., "Production of D-mannose from D-glucose by co-expression of D-glucose isomerase and D-lyxose somerase in *Escherichia coli*", J. Sci. Food Agric. 2018: 98; pp. 4895-4902.
GenBank (NCBI) Sequence WP_068757330.1 HAD Family Phosphatase [Thermobifida cellulosilytica] May 13, 2017.
Kuznetsova et al., "Functional Diversity of Haloacid Dehalogenase Superfamily Phosphatases from *Saacharomyces cerevisiae*", Journal of Biological Chemistry, Jun. 12, 2015; vol. 290, No. 30, pp. 18678-18698.
International Search Report and Written Opinion in International Application No. PCT/US2020/017708, dated May 5, 2020.

* cited by examiner

*Primary Examiner* — Marsha Tsay
(74) *Attorney, Agent, or Firm* — RAPHAEL BELLUM PLLC (57) ABSTRACT

Disclosed herein are improved processes for making mannose including the step of converting the M6P to mannose, catalyzed by a M6PP, using enzymes with higher activities compared to M6PPs previously used in a process to produce mannose.

18 Claims, 8 Drawing Sheets

Specification includes a Sequence Listing.

SEQUENCE LISTING

```
<160> NUMBER OF SEQ ID NOS: 2

<210> SEQ ID NO 1
<211> LENGTH: 223
<212> TYPE: PRT
<213> ORGANISM: Thermobifida cellulosilytica TB100

<400> SEQUENCE: 1
```

```
Met Ile Ser Asp Ser Asp Pro Gln Ile Pro Gln Ala Val Leu Phe Asp
1               5                   10                  15

Met Asp Gly Thr Leu Ile Asp Thr Glu Pro Met Trp Met Asp Thr Glu
                20                  25                  30

Ala Glu Val Ala Ala Ala Phe Gly Tyr Thr Trp Thr Ala Glu Asp Gln
            35                  40                  45

Gln Arg Cys Leu Gly Gly Ser Ala Ala Ala Val Ala Asp Leu Ile Ala
        50                  55                  60

Glu Arg Ser Gly Thr Arg Thr Pro Gln Ser Glu Ile Val Ala Met Leu
65                  70                  75                  80

Tyr Ala Ala Val Glu Arg Arg Met Ala Glu Gly Val Pro Val Arg Pro
                85                  90                  95

Gly Ala Lys Glu Leu Leu Thr Glu Leu Glu Ala Gln Gly Val Pro Met
            100                 105                 110

Ala Leu Val Thr Ser Thr Tyr Arg Ser Leu Leu Thr Val Ala Leu Arg
            115                 120                 125

Ala Ile Gly Glu His Tyr Phe Ala Val Ser Val Ala Gly Asp Glu Val
            130                 135                 140

Thr Arg Asn Lys Pro His Pro Glu Pro Tyr Leu Arg Ala Ala Arg Leu
145                 150                 155                 160

Leu Gly Val Asp Pro Arg Arg Cys Val Ala Val Glu Asp Ser Pro Thr
                165                 170                 175

Gly Val Ala Ser Ala Gln Ala Ala Gly Cys Thr Val Val Ala Val Pro
                180                 185                 190

His Met Ala Ser Val Pro Ala Ala Glu Arg Arg Tyr Val Val Gly Ser
            195                 200                 205

Leu Glu Glu Val Asp Leu Ala Trp Leu Arg Arg Val Ser Pro Ala
            210                 215                 220

<210> SEQ ID NO 2
<211> LENGTH: 6
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (3)..(5)
<223> OTHER INFORMATION: Xaa can be any naturally occurring amino acid

<400> SEQUENCE: 2

Gly Asp Xaa Xaa Xaa Asp
1               5
```

ENZYMATIC PRODUCTION OF MANNOSE

CROSS-REFERENCE TO RELATED APPLICATIONS

This application claims priority to U.S. Application Ser. No. 62/804,426, filed on Feb. 12, 2019, which is incorporated herein by reference in its entirety.

FIELD OF THE INVENTION

The invention relates to the field of biotechnology pertaining to D-mannose production. More specifically, the invention provides improved D-mannose preparation methods capable of enzymatically converting saccharides (e.g., polysaccharides, oligosaccharides, disaccharides, sucrose, D-glucose, and D-fructose) into D-mannose.

BACKGROUND

D-mannose (mannose hereafter) is a mildly sweet, naturally-occurring monosaccharide that is found in many fruits, vegetables, plant materials, and even the human body. Mannose boasts multiple health benefits and pharmaceutical applications. For example, mannose can be used to treat carbohydrate-deficient glycoprotein syndrome type 1b and, more commonly, urinary tract infections. Furthermore, mannose is a verified prebiotic, does not raise blood glucose levels, and shows anti-inflammatory properties. Additionally, it has been shown to enhance carcass yields in pigs and is a widely used auxiliary moisturizing agent for skin-care products. As such, mannose has a variety of applications in the pharmaceutical, cosmetic, consumable products (beverages, food products, dairy, confectionery, etc.), and livestock industries. However, due to mannose's high selling prices, its use in everyday products has been limited.

Currently, mannose is primarily produced through extraction from plants. Common methods include acid hydrolysis, thermal hydrolysis, enzymatic hydrolysis, microbial fermentation hydrolysis, and mixtures thereof. Less common methods include chemical and biological transformations. Overall, these methods suffer from harsh conditions, high capital expenditures, higher feedstock cost, costly separation of mannose from isomerization reactions, and relatively low product yields (15-35%).

There is a need to develop a cost-effective synthetic pathway for high-yield mannose production where at least one step of the process involves an energetically favorable chemical reaction. Furthermore, there is a need for production process where the process steps can be conducted in one tank or bioreactor. There is also a need for a process of mannose production that can be conducted at a relatively low concentration of phosphate, where phosphate can be recycled, and/or the process does not require using adenosine triphosphate (ATP) as a source of phosphate. There is also a need for a mannose production pathway that does not require the use of the costly nicotinamide adenosine dinucleotide (NAD(H)) coenzyme in any of the reaction steps International Patent Application Publication No. WO 2018/169957 describes an enzymatic synthesis of D-mannose, in a process that includes converting mannose 6-phosphate (M6P), catalyzed by to mannose, catalyzed by a mannose 6-phosphate phosphatase. However, despite improvements in enzymatic mannose production, there is still a desire and need for providing further improved processes of producing mannose that can, e.g., provide a higher yield with lower amounts of enzymes. There is a strong industrial and commercial interest in decreasing the cost of mannose production, and this decrease involves the use of a reduced amount of enzymes and use of combinations of enzymes that are more effective.

SUMMARY OF THE INVENTION

In one aspect, the invention provides an improved D-mannose preparation method capable of enzymatically converting saccharides (e.g., polysaccharides, oligosaccharides, disaccharides, sucrose, D-glucose, and D-fructose) into D-mannose. An improved process of the invention for the production of mannose from a saccharide includes a step of converting mannose-6-phosphate (M6P) to mannose, catalyzed by mannose-6-phoshpate phosphatase (M6PP), wherein the M6PP comprises an amino acid sequence having at least 90% sequence identity with SEQ ID NO: 1.

In some processes of the invention, mannose is prepared in a process with a step of converting fructose 6-phosphate (F6P) to mannose 6-phosphate (M6P), where the step is catalyzed by mannose 6-phosphate isomerase (M6PI). In some aspects, the process includes converting glucose 6-phosphate (G6P) to the F6P, where the step is catalyzed by phosphoglucoisomerase (PGI). In further aspects, G6P is converted to F6P then converted to M6P by one enzyme: bifunctional phosphoglucose/phosphomannose isomerase (PGPMI). In other aspects, a process for mannose synthesis also includes the step of converting glucose 1-phosphate (G1P) to the G6P, and this conversion step is catalyzed by phosphoglucomutase (PGM).

The saccharides used in any of the processes can be selected from the group consisting of a starch or its derivative, cellulose or its derivative, and sucrose. The starch or its derivative can be amylose, amylopectin, soluble starch, amylodextrin, maltodextrin, maltose, or glucose. In some improved processes of the invention, the process for preparing mannose involves converting starch to a starch derivative by enzymatic hydrolysis or by acid hydrolysis of starch. In other processes, a starch derivative is prepared by enzymatic hydrolysis of starch catalyzed by isoamylase, pullulanase, alpha-amylase, or a combination of two or more of these enzymes. Some processes of the invention can additionally involve adding 4-glucan transferase (4GT).

Other processes of the invention for preparing mannose further include a step of converting fructose to F6P, catalyzed by at least one enzyme. Other processes of the invention include a step of converting sucrose to the fructose, catalyzed by at least one enzyme. G6P to be used in processes for preparing mannose can also be generated by converting glucose to the G6P, catalyzed by at least one enzyme. Glucose can in turn be produced by converting sucrose to glucose, catalyzed by at least one enzyme.

Process of the invention are conducted at a temperature ranging from about 37° C. to about 85° C., at a pH ranging from about 5.0 to about 9.0, and/or for about 1 hour to about 48 hours, or as continuous reactions. In some embodiments, the steps of a process for preparing mannose are conducted in one bioreactor. In other aspects, the steps are conducted in a plurality of bioreactors arranged in series.

In some processes of the invention, the steps for preparing mannose are conducted ATP-free, NAD(H)-free, at a phosphate concentration from about 0.1 mM to about 150 mM, the phosphate is recycled, and/or the step of converting M6P to mannose involves an energetically favorable chemical reaction.

BRIEF DESCRIPTION OF THE FIGURES

FIG. 1 is a schematic diagram illustrating an enzymatic pathway converting starch or its derived products to mannose. The following abbreviations are used: aGP, alpha-glucan phosphorylase or starch phosphorylase; PGM, phosphoglucomutase; PGI, phosphoglucoisomerase; PGPMI, bifunctional phosphoglucose/phosphomannose isomerase; M6PI; mannose 6-phosphate isomerase, M6PP, mannose 6-phosphate phosphatase; IA, isoamylase; PA, pullulanase; MP, maltose phosphorylase; PPGK, polyphosphate glucokinase; and $P_i$, phosphate. In processes according to the invention, the M6PP comprises an amino acid sequence having at least 90% sequence identity with SEQ ID NO: 1.

FIG. 2 shows an enzymatic pathway converting cellulose or its derived products to mannose. The following abbreviations are used: CDP, cellodextrin phosphorylase; CBP, cellobiose phosphorylase; PPGK, polyphosphate glucokinase; PGM, phosphoglucomutase; PGI, phosphoglucoisomerase; PGPMI, bifunctional phosphoglucose/phosphomannose isomerase; M6PI, mannose 6-phosphate isomerase; M6PP, mannose 6-phosphate phosphatase; and $P_i$, phosphate. In processes according to the invention, the M6PP comprises an amino acid sequence having at least 90% sequence identity with SEQ ID NO: 1.

FIG. 3 is a schematic diagram illustrating an enzymatic pathway converting fructose to mannose. PPFK, polyphosphate fructokinase; M6PI, mannose 6-phosphate isomerase; M6PP, mannose 6-phosphate phosphatase; and $P_i$, phosphate. In processes according to the invention, the M6PP comprises an amino acid sequence having at least 90% sequence identity with SEQ ID NO: 1.

FIG. 4 is a schematic diagram illustrating an enzymatic pathway converting glucose to mannose. PPGK, polyphosphate glucokinase; PGI, phosphoglucoisomerase; PGPMI, bifunctional phosphoglucose/phosphomannose isomerase; M6PI, mannose 6-phosphate isomerase; M6PP, mannose 6-phosphate phosphatase; and $P_i$, phosphate. In processes according to the invention, the M6PP comprises an amino acid sequence having at least 90% sequence identity with SEQ ID NO: 1.

FIG. 5 shows an enzymatic pathway converting sucrose or its derived products to mannose. SP, sucrose phosphorylase; PPFK, polyphosphate fructokinase; PGM, phosphoglucomutase; PGI, phosphoglucoisomerase; PGPMI, bifunctional phosphoglucose/phosphomannose isomerase; M6PI, mannose 6-phosphate isomerase; M6PP, mannose 6-phosphate phosphatase; and $P_i$, phosphate. In processes according to the invention, the M6PP comprises an amino acid sequence having at least 90% sequence identity with SEQ ID NO: 1.

DETAILED DESCRIPTION

The invention generally relates to processes for the conversion of saccharides such as starch, cellulose, sucrose, glucose, and fructose and their derived products to mannose using cell-free enzyme cocktails. In contrast to cell-based manufacturing methods, the invention involves a cell-free preparation of mannose, has relatively high reaction rates due to the elimination of the cell membrane, which often slows down the transport of substrate/product into and out of the cell. It also has a final product free of nutrient-rich fermentation media/cellular metabolites.

The invention relates to improved processes for making mannose including the step of converting M6P to mannose, catalyzed by a M6PP with improved activity compared M6PPs previously used in a process to produce mannose. See e.g., International Patent Application Publication WO2018/169957, disclosing M6PP from *Tepidimonas fonticaldi* (Uniprot ID A0A1A6DSI3), M6PP from *Thermomonas hydrothermalis* (Uniprot ID A0A1M4UN08), and M6PP from *Sulfurivirga caldicuralii* (Uniprot ID A0A1N6FCW3). Using enzymes with higher activities allows for using lower amounts of enzymes, thereby reducing the cost of the overall process.

In the improved processes of the invention, the M6PPs have a higher activity compared to that of the previously disclosed M6PP from *Sulfurivirga caldicuralii* (Uniprot ID A0A1N6FCW3). Preferably, M6PPs used in the processes of the invention have an enzymatic activity improved by at least 10%, at least 30%, at least 80%, at least 100%, at least 150%, at least 300%, or at least 400%, relative to the activity of M6PP from *Sulfurivirga caldicuralii* (Uniprot ID A0A1N6FCW3). For instance, as shown in Example 1, M6PP from *Thermobifida cellulosilytica* TB100 (Uniprot ID A0A147K118) has enzymatic activity improved by approximately 215% relative to M6PP from *Sulfurivirga caldicuralii* (Uniprot ID A0A1N6FCW3). The examples below provide protocols to those skilled in the art for determining activity of M6PPs, which involve incubating the enzyme with its substrate, and then measuring the amounts of reactants and products via HPLC. Measurements of relative activities any two enzymes are performed under identical reaction conditions such as buffer, pH, temperature, etc.

M6PPs used in the processes of the invention are specific for M6P. For M6PP, specific means having a higher dephosphorylation activity on M6P over other phosphorylated monosaccharides in the process. For instance, M6PP has a higher dephosphorylation activity on M6P than on, for example G1P, G6P, and F6P.

Examples of M6PPs for use in the processes of the invention include M6PP from *Thermobifida cellulosilytica* TB100 (Uniprot ID A0A147K118), with the amino acid sequence as set forth in SEQ ID NO: 1, and M6PPs having at least 90%, at least 95%, at least 97%, at least 99%, or 100% amino acid sequence identity to SEQ ID NO: 1. The amino acid sequence SEQ ID NO:1 is as follows:

MISDSDPQIPQAVLFDMDGTLIDTEPMWMDTEAEVAAAFGYTWTAED

QQRCLGGSAAAVADLIAERSGTRTPQSEIVAMLYAAVERRMAEGVPV

RPGAKELLTELEAQGVPMALVTSTYRSLLTVALRAIGEHYFAVSVAG

DEVTRNKPHPEPYLRAARLLGVDPRRCVAVEDSPTGVASAQAAGCTV

VAVPHMASVPAAERRYVVGSLEEVDLAWLRRVSPA.

A process according to the invention for the improved production of mannose from a saccharide includes a step of converting M6P to mannose using a mannose-6-phoshpate phosphatase (M6PP), where the M6PP comprises an amino acid sequence having at least 90% sequence identity to SEQ ID NO: 1. In a preferred process, the M6PP has the amino acid sequence as set forth in SEQ ID NO: 1.

Preferably, an M6PP to convert M6P to mannose contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd β-strand of the Rossmanoid fold, and a GDXXXD (SEQ ID NO: 2) signature at the end of the 4th β-strand of the Rossmanoid fold.

In one embodiment, a process for preparing mannose from a saccharide according to the invention also includes the step of enzymatically converting F6P to M6P, catalyzed by mannose 6-phosphate isomerase, M6PI. Exemplary M6PI which may be used include M6PI from *Pseudonocardia thermophila* (Uniprot ID A0A1M6TLY7), M6PI from *Caldithrix abyssi* (Uniprot ID H1XQS6), M6PI from *Myceliophthora thermophila* (Uniprot ID G2Q982), and M6PI from *Treponema* caldarium (Uniprot ID F8F1Z8). See e.g., International Patent Application Publication WO2018/169957.

Some processes for preparing mannose from a saccharide according to the invention additionally include the step of enzymatically converting glucose 6-phosphate (G6P) to F6P, where the step is catalyzed by phosphoglucose isomerase (PGI). Exemplary PG's which may be used include those disclosed in International Patent Application Publication WO2017/059278: PGI from *Clostridium thermocellum* (Uniprot ID A3DBX9) and PGI from *Thermus thermophilus* (Uniprot ID Q5SLL6).

In other embodiments, the process for preparing mannose additionally includes the step of converting glucose 1-phosphate (G1P) to G6P, where the step is catalyzed by phosphoglucomutase (PGM), for example, PGM from *Thermococcus kodakaraensis* (Uniprot ID Q68BJ6)), disclosed in International Patent Application Publication WO2017/059278.

In further embodiments, the process for preparing mannose includes the conversion of G6P to F6P to M6P, where this step is catalyzed by bifunctional phosphoglucose/phosphomannose isomerase (PGPMI). Examples of PGPMIs include, but are not limited to PGPMI from *Syntrophothermus lipocalidus* (Uniprot ID D7CPH7), PGPMI from *Schleiferia thermophila* (Uniprot ID A0A085L170), and PGPMI from *Thermodesulfobium narugense* (Uniprot ID M1E6Z3).

Figure 2:
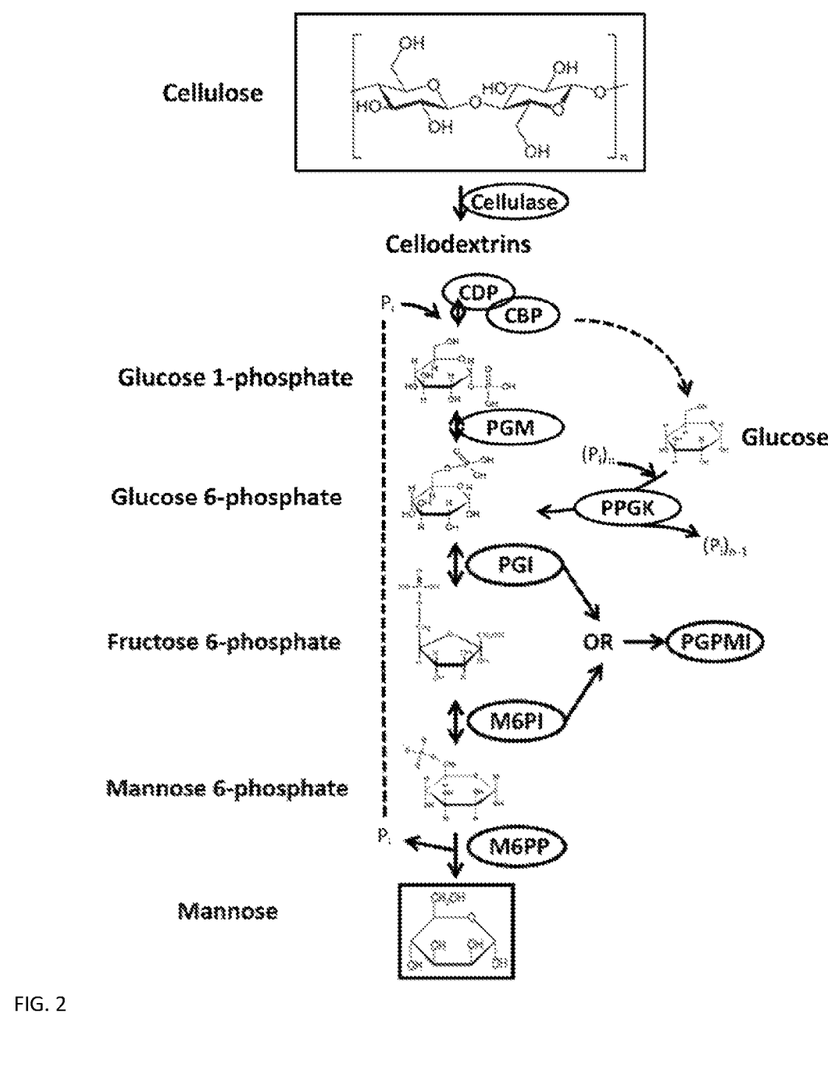
Figure 3:
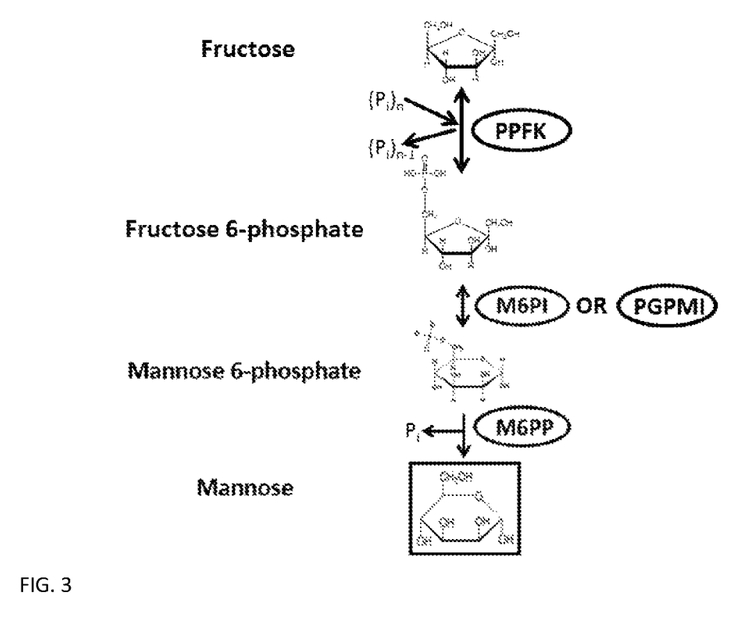
Figure 4:
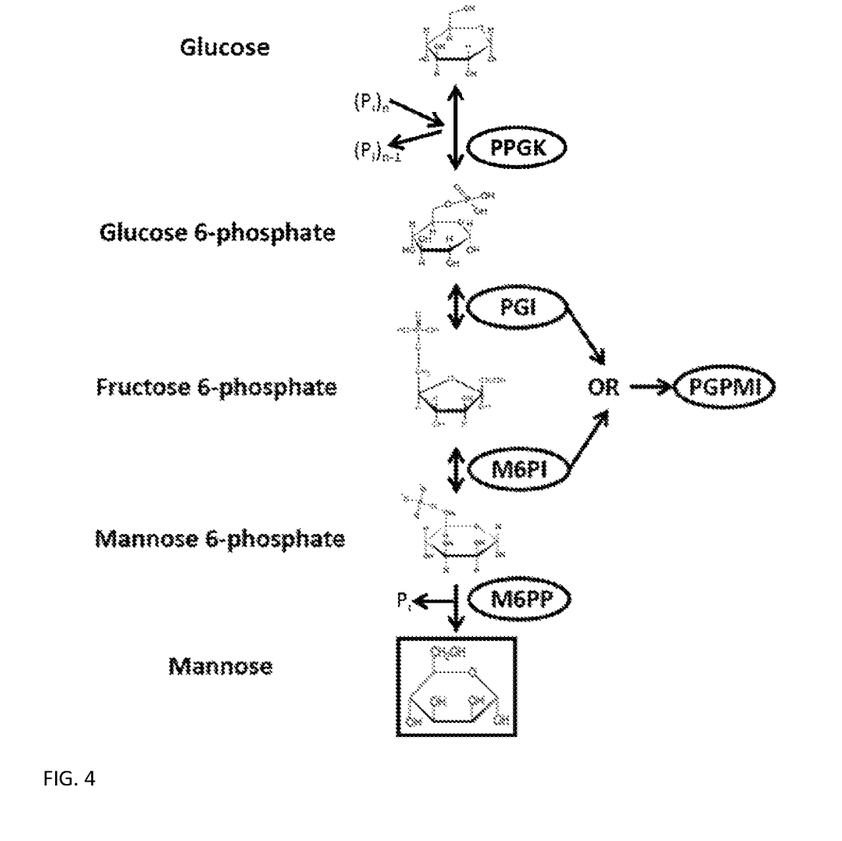
Figure 5:
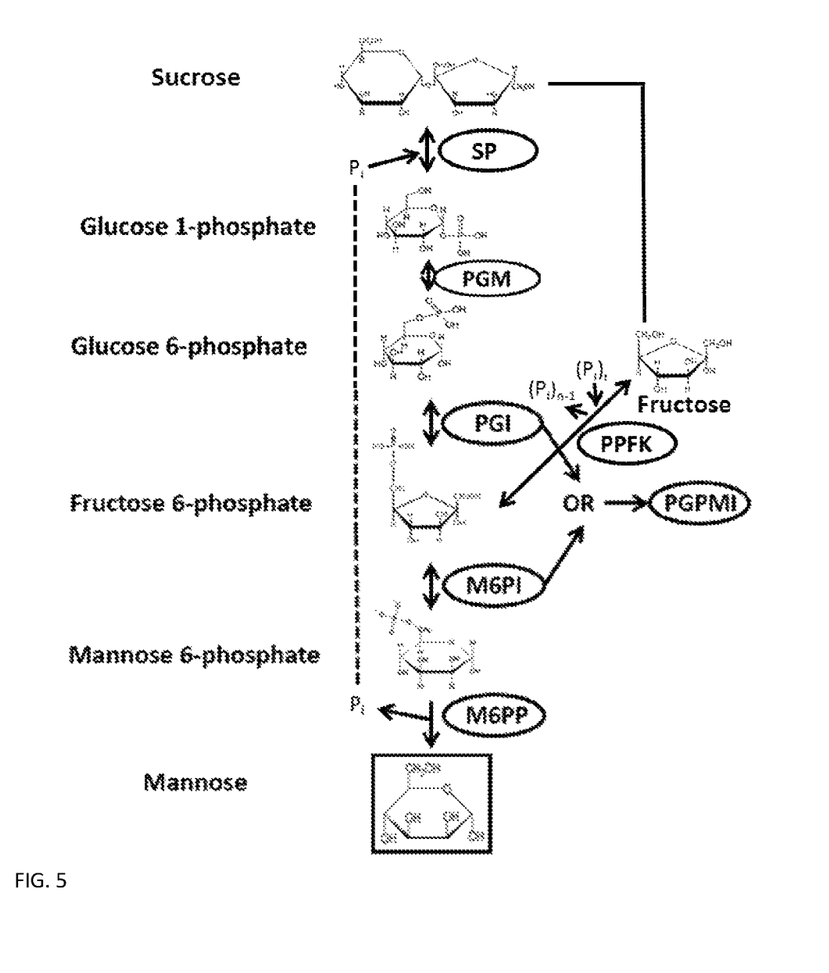

Additionally, the processes according to the invention may further comprise the step of converting a saccharide to the G1P, where the step is catalyzed by at least one enzyme, and the saccharide is selected from the group consisting of a starch or derivative thereof (FIG. 1), cellulose or a derivative thereof (FIG. 2), fructose (FIG. 3), glucose (FIG. 4), and sucrose (FIG. 5). The enzyme or enzymes used in the step of converting a saccharide to the G1P in the processes according to the invention can be alpha-glucan phosphorylase (αGP), maltose phosphorylase, sucrose phosphorylase, cellodextrin phosphorylase, cellobiose phosphorylase, and/or cellulose phosphorylase, and mixtures thereof. The choice of the enzyme or enzyme combination depends on the saccharide used in the process.

Cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

In certain processes according to the invention, cellulose and its derived products can be converted to mannose through a series of steps. See FIG. 2. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to M6P catalyzed by M6PI; and converting M6P to mannose catalyzed by M6PP. Alternatively, in the previous pathway the conversion of G6P to F6P to M6P can be catalyzed by PGPMI. In this process, the phosphate ions can be recycled by the step of converting cellodextrin and cellobiose to G1P. In some embodiments, polyphosphate and polyphosphate glucokinase (PPGK) can be added to the process, thus increasing yields of mannose by phosphorylating the degradation product glucose to G6P.

Several enzymes may be used to hydrolyze solid cellulose to water-soluble cellodextrins and cellobiose. Such enzymes include endoglucanase and cellobiohydrolase, but not including beta-glucosidase (cellobiase). Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partially hydrolyzed by using concentrated acids, including hydrochloric acid, sulfuric acid, phosphoric acid and their combinations.

When the saccharides include cellobiose, and the enzymes contain cellobiose phosphorylase, G1P is generated from cellobiose by cellobiose phosphorylase. When the saccharides contain cellodextrins and the enzymes include cellodextrin phosphorylase, G1P is generated from cellodextrins by cellodextrin phosphorylase. When the saccharides include cellulose, and enzymes contain cellulose phosphorylase, the G1P is generated from cellulose by cellulose phosphorylase.

When the saccharides include maltose and the enzymes contain maltose phosphorylase, the G1P is generated from maltose by maltose phosphorylase. If the saccharides include sucrose, and enzymes contain sucrose phosphorylase, the G1P is generated from sucrose by sucrose phosphorylase.

When the saccharide is starch or a starch derivative, the derivative may be selected from the group consisting of amylose, amylopectin, soluble starch, amylodextrin, maltodextrin, maltose, and glucose, and mixtures thereof. In certain processes of the invention, the enzymes used to convert a saccharide to G1P contain aGP. In this step, when the saccharides include starch, the G1P is generated from starch by αGP; when the saccharides contain soluble starch, amylodextrin, or maltodextrin, the G1P is produced from soluble starch, amylodextrin, or maltodextrin by αGP. An example of αGP is αGP from *Thermotoga maritima* (Uniprot ID G4FEH8), disclosed in International Patent Application Publication WO2017/059278.

Some processes according to the invention may further comprise the step of converting starch to a starch derivative, where the starch derivative is prepared by enzymatic hydrolysis of starch or by acid hydrolysis of starch. In certain processes of the invention, maltose phosphorylase (MP) can be used to increase mannose yields by phosphorolytically cleaving the degradation product maltose into G1P and glucose. Alternatively, 4-glucan transferase (4GT) can be used to increase mannose yields by recycling the degradation products glucose, maltose, and maltotriose into longer maltooligosaccharides; which can be phosphorolytically cleaved by αGP to yield G1P. An example of 4GT is 4GT from *Thermococcus litoralis* (Uniprot ID O32462), disclosed in International Patent Application Publication WO2017/059278. In some processes of the invention, polyphosphate and polyphosphate glucokinase (PPGK) can be added to the process, thus increasing yields of mannose by phosphorylating the degradation product glucose to G6P.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

Where the processes use a starch derivative, the starch derivative can be prepared by enzymatic hydrolysis of starch catalyzed by isoamylase, pullulanase, α-amylase, or their combination. Corn starch contains many branches that impede αGP action. Isoamylase can be used to de-branch starch, yielding linear amylodextrin. Isoamylase-pretreated starch can result in a higher F6P concentration. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to mannose.

Mannose can also be produced from fructose. See FIG. 3. Processes according to the inventions can also comprise the step of converting fructose to F6P, wherein the step is catalyzed by at least one enzyme and, optionally, the step of converting sucrose to the fructose, wherein the step is catalyzed by at least one enzyme. For example, the process involves generating F6P from fructose and polyphosphate catalyzed by polyphosphate fructokinase (PPFK). The conversion of F6P to mannose is described above. The fructose can be produced, for example, by an enzymatic conversion of sucrose. The phosphate ions generated when M6P is converted to mannose can then be recycled in the steps of converting sucrose to G1P.

Mannose can also be produced from glucose. See FIG. 4. The process involves the steps of generating G6P from glucose and polyphosphate catalyzed by polyphosphate glucokinase (PPGK); converting G6P to F6P catalyzed by PGI; converting F6P to M6P catalyzed by M6PI; and converting M6P to mannose catalyzed by M6PP. Alternatively, the conversion of G6P to F6P to M6P can be catalyzed by PGPMI. The glucose can be produced, for example, by an enzymatic conversion of sucrose. See FIG. 5.

The phosphate ions generated when M6P is converted to mannose can then be recycled in the step of converting sucrose to G1P, especially if the process is conducted in a single reaction vessel. See FIG. 5. Additionally, PPFK and polyphosphate can be used to increase mannose yields by producing F6P from fructose generated by the phosphorolytic cleavage of sucrose by SP.

Figure 1:
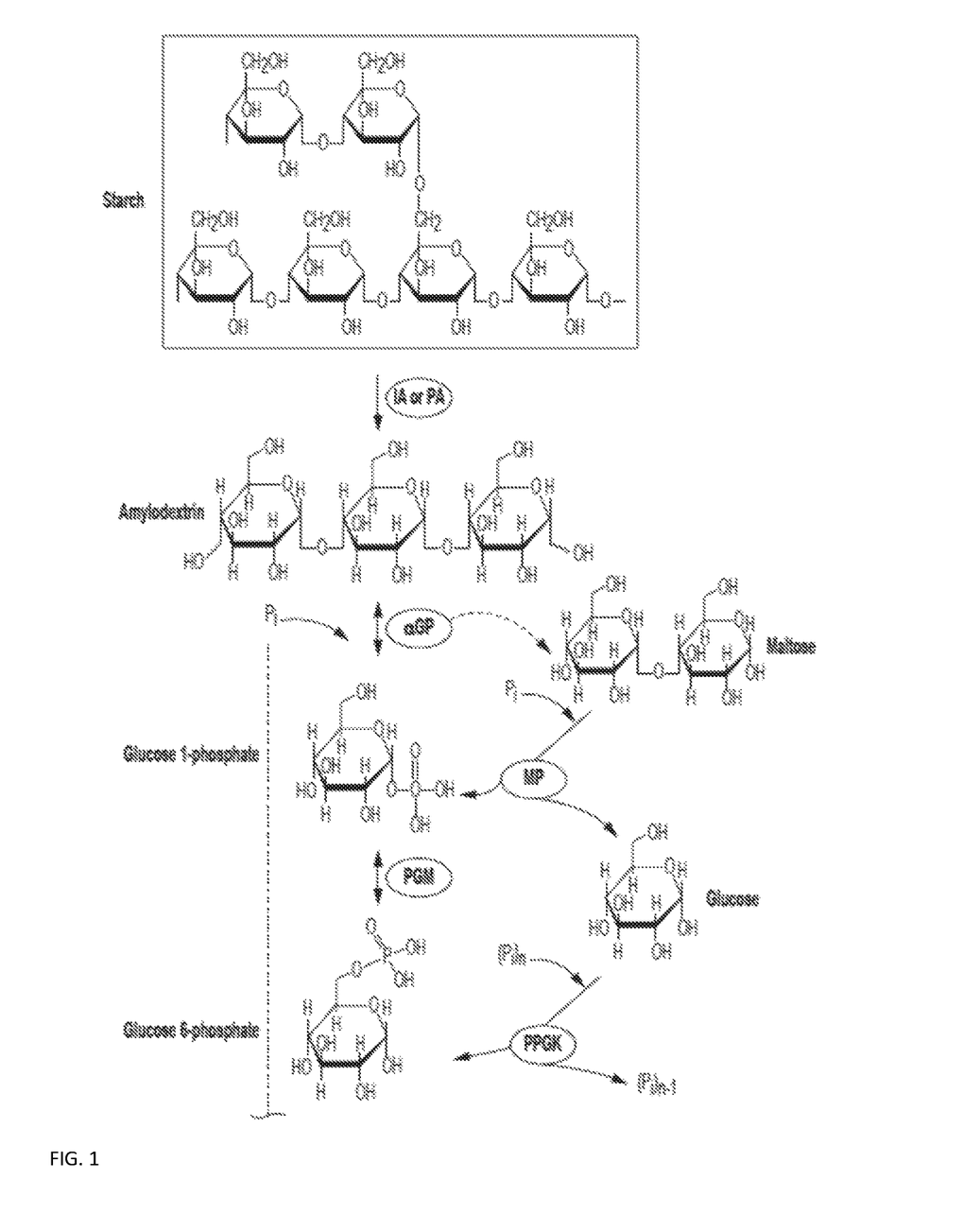

Processes for preparing mannose from a saccharide, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to M6P via mannose 6-phosphate isomerase (M6PI, EC 5.3.1.8), (v) converting G6P to M6P via bifunctional phosphoglucose/phosphomannose isomerase (PGPMI, EC 5.3.1.8 and 5.3.1.9), and (vi) converting M6P to mannose via M6PP. An example of the process where the saccharide is starch is shown in FIG. 1. In such a process, for example, the enzyme in step (i) may be αGP.

Typically, the ratios of enzyme units used in the process are 1:1:1:1:1 (αGP:PGM:PGI:M6PI:M6PP). An enzyme unit is the amount of enzyme needed to convert 1 umol of substrate to product in 1 minute. Accordingly, an enzyme with a higher activity will have a lower amount of enzyme, in terms of mg of enzyme per one enzyme unit, compared to an enzyme with a lower activity which catalyzes the same reaction. To optimize product yields, these ratios can be adjusted in any number of combinations. For example, a particular enzyme may be present in an amount about 2×, 3×, 4×, 5×, etc. relative to the amount of other enzymes.

A process for preparing mannose according to the invention may include the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

Processes to prepare mannose according the invention can be conducted in a single bioreactor or reaction vessel. Alternatively, the steps can also be conducted in a plurality of bioreactors, or reaction vessels, that are arranged in series. In a preferred process, the enzymatic production of mannose is conducted in a single reaction vessel.

The enzymes used in the invention may take the form of soluble, immobilized, assembled, or aggregated proteins. These enzymes could be adsorbed on insoluble organic or inorganic supports commonly used to improve functionality, as known in the art. These include polymeric supports such as agarose, methacrylate, polystyrene, or dextran, as well as inorganic supports such as glass, metal, or carbon-based materials. These materials are often produced with large surface-to-volume ratios and specialized surfaces that promote attachment and activity of immobilized enzymes. The enzymes might be affixed to these solid supports through covalent, ionic, or hydrophobic interactions. The enzymes could also be affixed through genetically engineered interactions such as covalent fusion to another protein or peptide sequence with affinity to the solid support, most often a polyhistidine sequence. The enzymes might be affixed either directly to the surface or surface coating, or they might be affixed to other proteins already present on the surface or surface coating. The enzymes can be immobilized all on one carrier, on individual carriers, or a combination of the two (e.g., two enzyme per carrier then mix those carriers). These variations can be mixed evenly or in defined layers to optimize turnover in a continuous reactor. For example, the beginning of the reactor may have a layer of αGP to ensure a high initial G1P concentration. Enzymes may be immobilized all on one carrier, on individual carriers, or in groups. These enzymes may be mixed evenly or in defined layers or zones to optimize turnover.

Any suitable biological buffer known in the art can be used in a process of the invention, such as HEPES, PBS, BIS-TRIS, MOPS, DIPSO, Trizma, etc. The reaction buffer for all embodiments can have a pH ranging from 5.0-9.0. More preferably, the reaction buffer pH can range from about 6.0 to about 7.3. For example, the reaction buffer pH can be 6.0, 6.2, 6.4, 6.6, 6.8, 7.0, 7.2, or 7.3.

The reaction buffer can also contain divalent metal cations. Examples of the metal ions include $Mg^{2+}$ and $Zn^{2+}$. The concentration of divalent metal ions can range from about 0 mM to about 150 mM, from about 0 mM to about 100 mM, from about 1 mM to about 50 mM, preferably from about 5 mM to about 50 mM, or more preferably from about 10 mM to about 50 mM. For instance, the reaction metal cation concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

The reaction temperature at which the process steps are conducted can range from 37-85° C. More preferably, the steps can be conducted at a temperature ranging from about 37° C. to about 85° C. The temperature can be, for example, about 40° C., about 45° C., about 50° C., about 55° C., or about 60° C. Preferably, the reaction temperature is about 50° C. In some processes of the invention, the reaction temperature is constant, and is not changed during the process.

The reaction time of the disclosed processes can be adjusted as necessary and can range from about 1 hour to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

The reaction can be run in batch or in a continuous process using a packed bed reactor or similar device. In the continuous process, a solution maltodextrin, for example, would be pumped through a bed of immobilized enzyme at such a rate that conversion to mannose would be complete when the solution leaves the column for downstream processing. For example, 200 g/L of maltodextrin can be pumped through a column packed with immobilized enzymes (maintained at, for example, 50° C.) such that when the maltodextrin leaves the column maximum mannose yield is achieved. This methodology offers greater volumetric productivity over batch methods. This limits the time the mannose product is in contact with the column and reaction conditions, which decreases chances of product degradation (e.g., potential hydroxymethylfurfural formation).

Phosphate ions ($P_i$) produced by M6PP dephosphorylation of M6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the mannose making processes.

For example, reaction phosphate concentrations can range from about 0 mM to about 300 mM, from about 0 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentrations result in decreased production costs due to low total phosphate and thus lowered cost of phosphate removal. It also prevents inhibition of M6PP by high concentrations of free phosphate and decreases the potential for phosphate pollution.

Figure 6:
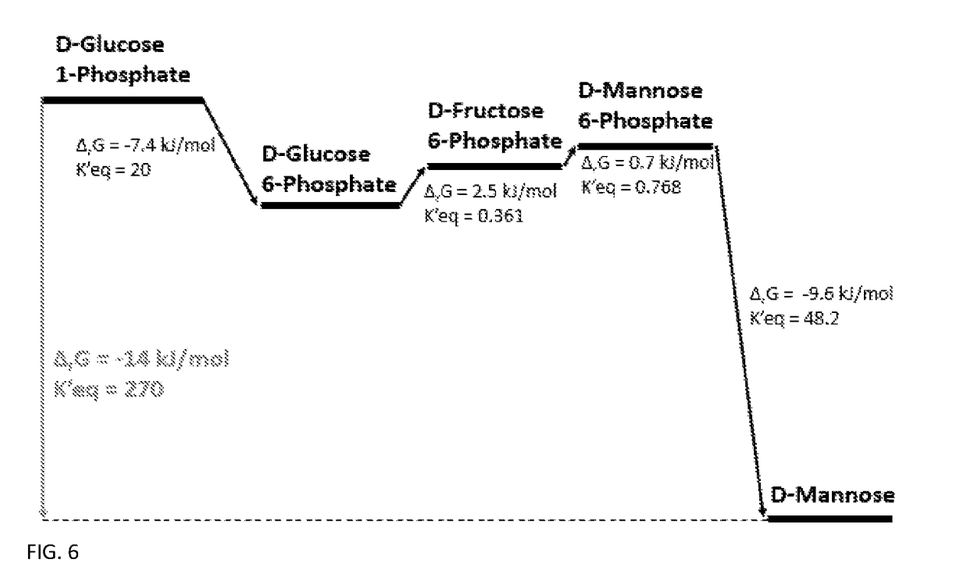
FIG. 6 shows the Reaction Gibbs Energy between intermediates based on formation Gibbs energy for the conversion of glucose 1-phosphate to mannose.

Furthermore, the processes disclosed herein can be conducted without added ATP as a source of phosphate, i.e., ATP-free. The processes can also be conducted without having to add NAD(H), i.e., NAD(H)-free. Other advantages also include the fact that at least one step of the disclosed processes for making mannose involves an energetically favorable chemical reaction. FIG. 6. While the use of enzymes with higher activities will not affect the overall energetics, the ability to use less enzymes in the improved processes is advantageous. The advantage is the reduction of the overall cost of enzyme in the total production cost of the product.

The processes according to the invention can achieve high yields due to the very favorable equilibrium constant for the overall reaction. FIG. 6. Theoretically, up to 99% yields can be achieved if the starting material is completely converted to an intermediate. Also, the step of converting M6P to mannose according to the invention is an irreversible phosphatase reaction, regardless of the feedstock. Therefore, mannose is produced with a very high yield.

Processes of the invention use low-cost starting materials and reduce production costs by decreasing costs associated with the feedstock and product separation. Starch, cellulose, sucrose and their derivatives are less expensive feedstocks than, for example, lactose. When mannose is produced from lactose, glucose and galactose and mannose are separated via chromatography, which leads to higher production costs.

Processes according to the invention allow for easy recovery of mannose, and separation costs are minimized. Preferably, in processes of the invention, the recovery of mannose is not via chromatographic separation. Following production of mannose in a continuous reaction, the product is instead passed through microfiltration, ion exchange (cation then anion, not mixed bed), concentration, crystallization, crystal isolation, and drying. Due to high yields of mannose, the crystallization step is all that is needed to purify mannose. To further purify mannose prior to crystallization, one can employ nanofiltration to eliminate the risk of enzyme being present in the crystallization process and to remove any unconverted dextrins that may co-crystallize with mannose or limit the recyclability of the mother liquor (maltodextrin, maltotetraose, maltotriose, maltose, etc.).

As shown in the examples below, a process for preparing mannose according to the invention includes the following steps: (i) converting a saccharide to G1P using one or more enzymes; (ii) converting G1P to G6P using PGM; (iii) converting G6P to F6P using PGI; (iv) converting F6P to M6P using M6PI, and (v) converting M6P to mannose using M6PP, where the M6PP comprises an amino acid sequence having at least 90% sequence identity with SEQ ID NO: 1. This process is preferably conducted in a single bioreactor or reaction vessel.

In some processes for producing mannose of the invention, the steps of (i) converting F6P to M6P using M6PI, and (ii) converting M6P to mannose using M6PP, where the M6PP comprises an amino acid sequence having at least 90% sequence identity with SEQ ID NO: 1, are conducted in a single bioreactor or reaction vessel. Preferably, an improved process for preparing mannose according to the invention includes the following steps: (i) converting a saccharide to G1P using one or more enzymes; (ii) converting G1P to G6P using PGM; (iii) converting G6P to F6P using PGI; (iv) converting F6P to M6P using M6PI, and (v) converting M6P to mannose using M6PP, where the M6PP comprises an amino acid sequence having at least 90% sequence identity with SEQ ID NO: 1 and where process steps (i)-(v) are conducted in a single bioreactor or reaction vessel. The process may incorporate one or more of the various process conditions discussed above.

EXAMPLES

Materials and Methods

All chemicals, including glucose 1-phosphate, magnesium chloride, sodium phosphate (mono and dibasic), are reagent grade or higher and purchased from Sigma-Aldrich (St. Louis, MO, USA) or Fisher Scientific (Pittsburgh, PA, USA), unless otherwise noted. *E. coli* BL21 (DE3) (Sigma-Aldrich, St. Louis, MO, USA) was used as a host cell for recombinant protein expression. ZYM-5052 media including 50 mg L-1 kanamycin was used for *E. coli* cell growth and recombinant protein expression.

Production and Purification of Recombinant Enzymes

The *E. coli* BL21 (DE3) strain harboring a protein expression plasmid (pET28a) was incubated in a 1-L Erlenmeyer flask with 100 mL of ZYM-5052 media containing 50 mg $L^{-1}$ kanamycin. Cells were grown at 37° C. with rotary shaking at 220 rpm for 16-24 hours. The cells were harvested by centrifugation at 12° C. and washed once with either 20 mM HEPES (pH 7.5) containing 50 mM NaCl and 5 mM $MgCl_2$ (heat precipitation) or 20 mM HEPES (pH 7.5) containing 300 mM NaCl and 5 mM imidazole (Ni purification). The cell pellets were re-suspended in the same buffer and lysed by sonication. After centrifugation, the target proteins in the supernatants were purified. His-tagged proteins were purified by the Profinity IMAC Ni-Charged Resin (Bio-Rad, Hercules, CA, USA). Heat precipitation at 50-80° C. for 5-30 min was used to purify thermostable enzymes. The purity of the recombinant proteins was examined by sodium dodecyl sulfate polyacrylamide gel electrophoresis (SDS-PAGE).

Example 1: WO 2018/169957 A1 M6PP Relative Activities

The conversion of G6P to mannose using the following enzymes, PGI (Uniprot ID Q5SLL6), PMI (Uniprot ID F8F1Z8), and M6PP (Uniprot IDs A0A1A6DSI3, A0A1M4UN08, and A0A1N6FCW3), was compared in order to determine relative M6PP rates. A 0.20 mL reaction mixture containing 38.5 mM G6P, 50 mM HEPES pH 7.2, 5 mM $MgCl_2$, 0.05 g/L PGI, 0.06 g/L PMI, and 0.3 g/L M6PP was incubated at 50° C. for 3 hours. M6PP is the rate limiting enzyme in this cascade reaction.

The reaction was stopped via filtration of enzyme with a Vivaspin 2 concentrator (10,000 MWCO) and analyzed via HPLC (Agilent 1100 series) using an Agilent Hi-Plex H-column and refractive index detector. The sample was run in 5 mM $H_2SO_4$ at 0.6 mL/min for 15.5 minutes at 65° C. Results show that Uniprot ID A0A1N6FCW3 is the most efficient M6PP from WO 2018/169957 A1 (Table 1).

TABLE 1

Relative activities of previously disclosed M6PPs

| M6PP Uniprot ID | Relative activity (%) |
|---|---|
| A0A1A6DSI3 | 45 |
| A0A1M4UN08 | 49 |
| A0A1N6FCW3 | 100 |

Example 2: M6PP with Higher Activity

The conversion of G1P to mannose using the following enzymes, PGM (Uniprot ID A0A150LLZ1), PGI (Uniprot ID Q5SLL6), PMI (Uniprot ID H1XQS6) and M6PP (Uniprot ID A0A1N6FCW3), was compared with the conversion of G1P to mannose with the enzyme useful in the improved processes of the invention, M6PP (Uniprot ID A0A147K118). A 0.20 mL reaction mixture containing 38.5 mM G1P, 50 mM HEPES pH 7.2, 5 mM $MgCl_2$, 0.05 g/L PGM, 0.05 g/L PGI, 0.05 g/L PMI, and 0.05 g/L M6PP was incubated at 50° C. for 0.5 hours. M6PP is the rate limiting enzyme in this cascade reaction.

Figure 7:
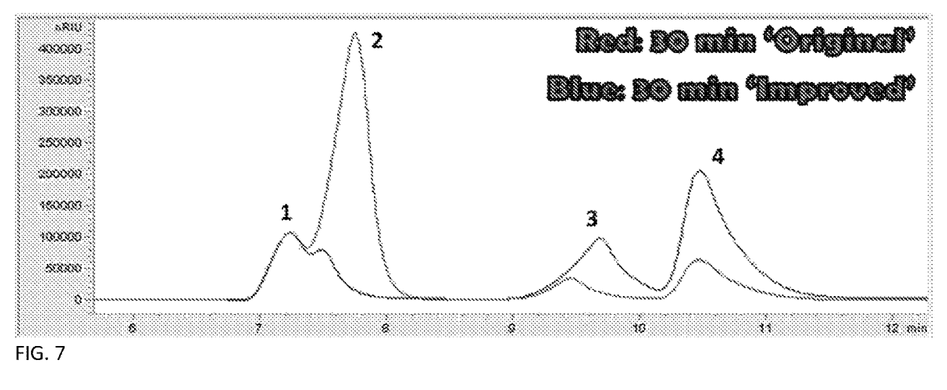
FIG. 7 shows the conversion of G1P to mannose measured via HPLC chromatogram as described in Example 1. 1=Void peak; 2=Phosphorylated sugars (G1P+G6P+F6P); 3=Inorganic Phosphate; 4=Mannose.

The reaction was stopped via filtration of enzyme with a Vivaspin 2 concentrator (10,000 MWCO) and analyzed via HPLC (Agilent 1100 series) using an Agilent Hi-Plex H-column and refractive index detector. The sample was run in 5 mM $H_2SO_4$ at 0.6 mL/min for 15.5 minutes at 65° C. Results show a 3.2-fold improvement in mannose production with the enzyme of the improved process over the previously disclosed enzymes (FIG. 7 and Table 2). Table 3 shows normalized relative activity comparing the previously disclosed M6PPs with M6PP (Uniprot ID A0A147KII8).

TABLE 2

Improved M6PP Activity

| M6PP Uniprot ID | Relative activity (%) |
|---|---|
| A0A1N6FCW3 | 100 |
| A0A147KII8 | 320 |

TABLE 3

Normalized Relative Activity of M6PPs

| M6PP Uniprot ID | Relative activity (%) |
|---|---|
| A0A1A6DSI3 | 45 |
| A0A1M4UN08 | 49 |
| A0A1N6FCW3 | 100 |
| A0A147KII8 | 320 |

What is claimed is:

1. An improved enzymatic process for the production of mannose from a saccharide, the improvement comprising converting mannose 6-phosphate (M6P) to mannose catalyzed by a mannose-6-phosphate phosphatase (M6PP), wherein the M6PP comprises the amino acid sequence as set forth in SEQ ID NO: 1,
   wherein the mannose yield is at least three-fold more than the mannose yield produced by catalyzing the conversion of M6P to mannose catalyzed by an M6PP from *Sulfurivirga caldicuralii* under equivalent process conditions.

2. The process of claim 1, further comprising a step of converting fructose-6-phosphate (F6P) to mannose 6-phosphate (M6P) catalyzed by a mannose 6-phosphate isomerase (M6PI).

3. The process of claim 2, further comprising a step of converting glucose 6-phosphate (G6P) to the F6P, wherein the step is catalyzed by a phosphoglucose isomerase (PGI).

4. The process of claim 3, further comprising a step of converting glucose 1-phosphate (G1P) to the G6P, wherein the step is catalyzed by a phosphoglucomutase (PGM).

5. The process of claim 4, further comprising a step of converting a saccharide to the G1P, wherein the step is catalyzed by at least one enzyme, wherein the saccharide is selected from the group consisting of a starch, a starch derivative, cellulose, a cellulose derivative, and sucrose.

6. The process of claim 5, wherein the at least one enzyme is selected from the group consisting of alpha-glucan phosphorylase (aGP), maltose phosphorylase, sucrose phosphorylase, cellodextrin phosphorylase, cellobiose phosphorylase, and cellulose phosphorylase.

7. The process of claim 5, wherein the saccharide is starch or a derivative thereof selected from the group consisting of amylose, amylopectin, soluble starch, amylodextrin, maltodextrin, maltose, and glucose.

8. The process of claim 7, further comprising a step of converting starch to a starch derivative wherein the starch derivative is prepared by enzymatic hydrolysis of starch or by acid hydrolysis of starch.

9. The process of claim 8, further comprising a step transglycosylating the starch derivative, catalyzed by a 4-glucan transferase (4GT).

10. The process of claim 9, wherein the starch derivative is prepared by enzymatic hydrolysis of starch catalyzed by an isoamylase, a pullulanase, an alpha-amylase, or a combination thereof.

11. The process claim 2, further comprising:
a step of converting fructose to the F6P, wherein the step is catalyzed by at least one enzyme; and, optionally, a step of converting sucrose to the fructose, wherein the step is catalyzed by at least one enzyme.

12. The process of claim 3, further comprising:
a step of converting glucose to the G6P, wherein the step is catalyzed by at least one enzyme; and, optionally, a step of converting sucrose to the glucose, wherein the step is catalyzed by at least one enzyme.

13. The process of claim 1, wherein the conversion of M6P to mannose is preceded by the steps of:
(i) converting a saccharide to glucose 1-phosphate (G1P) catalyzed by one or more enzymes, wherein the saccharide is selected from the group consisting of starch, one or more derivatives of starch, or a combination thereof;
(ii) converting G1P to glucose 6-phosphate (G6P) catalyzed by a phosphoglucomutase (PGM);
(iii) converting G6P to fructose 6-phosphate (F6P) catalyzed by a phosphoglucoisomerase (PGI); and
(iv) converting the F6P to mannose 6-phosphate (M6P) catalyzed by a mannose 6-phosphate isomerase (M6PI),
wherein all process steps are conducted as a continuous cascade reaction in a single reaction vessel.

14. The process of claim 13, wherein the continuous cascade reaction process steps are conducted under at least one of the following process conditions:
at a temperature ranging from 37° C. to 85° C.,
at a pH ranging from 5.0 to 9.0, or
for 1 hour to 48 hours.

15. The process of claim 13, wherein the continuous cascade reaction process steps are conducted under at least one of the following process conditions:
without adenosine triphosphate (ATP) as a source of phosphate,
without nicotinamide adenosine dinucleotide,
at a phosphate concentration from 0.1 mM to 150 mM,
at a $Mg^{2+}$ concentration from 0.1 mM to 50 mM
where phosphate is recycled, and
where at least one step of the process involves an energetically favorable chemical reaction.

16. The process of claim 15, wherein phosphate ions produced by M6PP dephosphorylation of M6P are recycled in the process step of converting a saccharide to G1P.

17. The process of claim 15, wherein the step of converting M6P to mannose is an energetically favorable, irreversible phosphatase reaction.

18. The process of claim 13, wherein the derivatives of starch are selected from the group consisting of amylose, amylopectin, soluble starch, amylodextrin, maltodextrin, maltotriose, maltose, and glucose.

* * * * *